United States Patent
Philippe

(10) Patent No.: US 6,306,376 B1
(45) Date of Patent: Oct. 23, 2001

(54) USE OF ARBUTIN MONOESTERS AS DEPIGMENTING AGENTS

(75) Inventor: Michel Philippe, Wissous (FR)

(73) Assignee: L'Oreal, Paris (FR)

(*) Notice: Subject to any disclaimer, the term of this patent is extended or adjusted under 35 U.S.C. 154(b) by 0 days.

(21) Appl. No.: 09/112,001

(22) Filed: Jul. 8, 1998

(30) Foreign Application Priority Data

Jul. 8, 1997 (FR) .................................................. 97 08674

(51) Int. Cl.⁷ .......................... A61K 31/70; A61K 7/135; A61K 7/44
(52) U.S. Cl. ................. 424/62; 424/60; 514/25; 536/5; 536/107
(58) Field of Search ................. 514/25; 536/4.1, 536/107; 424/62, 60

(56) References Cited

U.S. PATENT DOCUMENTS

| 4,526,779 | * | 7/1985 | Hashimoto | 424/62 |
| 5,346,693 | * | 9/1994 | Pilleux et al. | 424/62 |
| 5,424,406 | * | 6/1995 | Tsujihara et al. | 536/4.1 |
| 5,631,002 | * | 5/1997 | Yagi et al. | 424/62 |
| 5,731,292 | * | 3/1998 | Tsujihara et al. | 514/25 |
| 5,834,518 | * | 11/1998 | Galey et al. | 514/566 |
| 5,869,031 | * | 2/1999 | Tarroux et al. | 424/62 |

FOREIGN PATENT DOCUMENTS

| 0 597 776 | 5/1994 | (EP) . |
| 2 577 805 | 8/1986 | (FR) . |

* cited by examiner

*Primary Examiner*—Sabiha Qazi
(74) *Attorney, Agent, or Firm*—Oblon, Spivak, McClelland, Maier & Neustadt, P.C.

(57) ABSTRACT

Arbutin monoesters are employed in a composition for topical application, as a depigmenting and/or bleaching agent for human skin, hair and/or head hair.

The invention relates to a method of manufacturing a composition of at least one arbutin monoester in a physiologically acceptable medium for depigmenting and/or bleaching human skin, hair and/or head hair.

14 Claims, No Drawings

USE OF ARBUTIN MONOESTERS AS DEPIGMENTING AGENTS

BACKGROUND OF THE INVENTION

1. Field of the Invention

The present invention relates to the use of arbutin monoesters as depigmenting or bleaching agents in a composition for topical application, in particular a cosmetic and/or dermatological composition, as well as to the use of these arbutin esters in and/or for the manufacture of a cosmetic and/or dermatological composition, as a tyrosinase inhibitor and/or as a melanin-synthesis inhibitor. More particularly, the present invention relates to a process for depigmenting and/or bleaching the skin, hairs and head hair, using such arbutin monoesters.

2. Description of the Background

The color of the skin depends on different factors and, in particular, the seasons of the year, race and sex, and it is mainly determined by the concentration of melanin produced by the melanocytes. In addition, at different periods in their lives, certain individuals develop darker and/or more colored blemishes on the skin, especially on the hands, making the skin non-uniform in appearance. These blemishes are also caused by a large concentration of melanin in the keratinocytes at the skin surface.

In the same way, the color of hair and head hair is attributable to the presence of melanin. When hair or head hair is dark, certain people wish to have them lighter. This is particularly advantageous for hairs which are less visible when they are light than when they are dark.

For several years, a desired objective has been to decrease and/or slow down the production of melanin in order to depigment or bleach the skin, by acting on one or more of the points in the intracellular biochemical synthesis of melanin.

The mechanism for the formation of skin pigmentation, and pigmentation of hair and head hair, that is to say, the formation of melanin, is particularly complex and schematically involves the following main steps:

Tyrosine→Dop→Dopaquinone→Dopachrome→Melanin

Tyrosinase (monophenol dihydroxyl phenylalanine: oxygen oxidoreductase EC 1.14.18.1)) is the essential enzyme involved in this reaction sequence. It especially catalyses the reaction for the conversion of tyrosine into dopa (dihydroxyphenylalanine) and the reaction for the conversion of dopa into dopaquinone. This tyrosinase acts only when it is in the mature state, under the action of certain biological factors.

A substance is recognized as being depigmenting if it acts directly on the viability of the epidermal melanocytes in which melanogenesis takes place and/or if it interferes with one of the steps in the biosynthesis of melanin either by inhibiting one of the enzymes involved in melanogenesis or by becoming intercalated as a structural analogue of one of the chemical compounds in the melanin synthesis chain, whereby this chain may be blocked and ensure the depigmentation.

The substances most commonly used as depigmenting agents are, more particularly, hydroquinone and its derivatives, in particular its ethers such as hydroquinone monomethyl ether and monoethyl ether. Although they have a certain level of efficacy, these compounds are unfortunately not free of side effects on account of their toxicity, which can make them difficult or even hazardous to use. This toxicity arises from the fact that they interfere with fundamental mechanisms of melanogenesis, by killing cells which then risk disrupting their biological environment and which consequently force the skin to eliminate them by producing toxins.

Thus, hydroquinone is a compound which is particularly irritant and cytotoxic to melanocytes, and whose total or partial replacement has been envisaged by many investigators.

In order to overcome the drawbacks mentioned above, it has been envisaged, for example, to use derivatives of active compounds. Thus, U.S. Pat. No. 4,526,779 describes the use of fatty acid esters of hydroquinone as depigmenting agents. Unfortunately, these derivatives are less active than hydroquinone.

Substances have been sought which are not involved in the mechanism of melanogenesis, but which act upstream on tyrosinase by preventing its activation, and are consequently much less toxic. Kojic acid is commonly used as tyrosinase-activation inhibitor, this acid complexing the copper present in the active site of the enzyme. Unfortunately, this compound can give rise to allergic reactions ("Contact allergy to kojic acid in skin care products", M. Nakagawa et al, in Contact Dermatitis, January 95, Vol. 42 (1), pp. 9–13). In addition, this compound is unstable in solution, which somewhat complicates the manufacture of a composition containing it.

It is most particularly desired to use harmless topical depigmenting substances which are of good efficacy, in order to treat regional hyperpigmentations caused by melanocyte hyperactivity, such as idiopathic melasmas, occurring during pregnancy ("pregnancy mask" or chloasma) or during oestro-progestative contraception, localized hyperpigmentations caused by hyperactivity and proliferation of benign melanocytes, such as senile pigmentation marks known as actinic lentigo, accidental hyperpigmentations or depigmentations, possibly due to photosensitization or to post-lesional cicatrization, as well as certain leukodermias, such as vitiligo. For the latter, in which the cicatrizations can result in a scar which gives the skin a whiter appearance and leukodermias, failing being able to repigment the damage to the skin, the regions of residual normal skin are depigmented in order to give the skin as a whole a uniform white complexion.

Thus, there is a need for an agent for bleaching human skin, hairs and/or head hair which acts as effectively as known agents, but which does not exhibit their drawbacks, i.e. which is non-irritant, non-toxic and/or non-allergenic to the skin and which is stable in a composition.

SUMMARY OF THE INVENTION

Accordingly, one object of the present invention is to provide an agent for the bleaching or depigmentation of human skin and/or hair which is not toxic, non-irritating and non-allergenic to the skin and which is stable in a formulation.

Briefly, this object and other objects of the present invention as hereinafter will become more readily apparent can be attained in a method of manufacturing a cosmetic and/or dermatological composition by combining at least one arbutin monoester of formula (I):

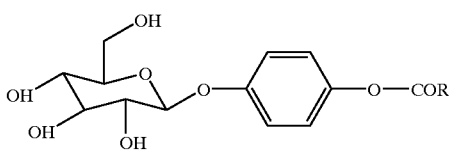

(I)

in which R is a linear or branched, saturated $C_{5-21}$ alkyl group, a $C_{5-21}$ alkenyl group or a $C_{9-2}$, alcapolyenyl group with physiologically acceptable topical excipients for depigmenting and/or bleaching human skin and/or for removing pigmentation marks from the skin and/or for depigmenting hair and/or head hair.

Another embodiment of the invention is a method of treating human skin or hair with a composition containing at least one arbutin monoester of formula (I).

DETAILED DESCRIPTION OF THE PREFERRED EMBODIMENTS

Applicant has found, unexpectedly, that certain arbutin esters have the property of inhibiting the synthesis of melanin and are thus capable of acting on skin pigmentation and marks without toxicity. This is all the more surprising given that the free aromatic hydroxyl function of arbutin, which is important in the enzymatic recognition, is, in these compounds, masked by an ester residue, and given that the depigmenting activity is nevertheless conserved, whereas this same aromatic hydroxyl blocked by a sugar residue such as glucose no longer allows the molecule to retain its depigmenting activity. Thus, for example, di-o-β-glucopyranose-1,4-hydroquinone has no depigmenting activity.

It is noted that EP 0 597 776 describes the compounds of the invention and their applications in the cosmetics, pharmaceutical, buccodental or food sectors. However, it does not attribute a depigmenting activity to these compounds.

The present invention is directed to the use of the present arbutin esters in and/for the manufacture of a cosmetic and/or dermatological composition as a tyrosinase inhibitor and/or the synthesis of melanin.

Another embodiment of the invention is a cosmetic and/or dermatological process for depigmenting and/or bleaching human skin, hair or head hair, which consists in applying an ester of formula (I) in a physiologically acceptable medium to the skin, hair or head hair.

The linear or branched alkyl (R) group preferably contains from 6–18 carbon atoms. Preferably, the RCO group, in which R is an alkyl group is selected from hexanoyl, decanoyl, dodecanoyl and hexadecanoyl groups.

The term alkenyl (or alcoylene) group is understood to refer to an unsaturated group containing ethylenic unsaturation. The alkenyl group preferably contains from 6–18 carbon atoms. Preferably, the RCO group, in which R is an alkenyl group is the oleoyl group.

The term alcapolyenyl group is understood to refer to an unsaturated radical containing several ethylenically unsaturated groups, in particular having two or three ethylenically unsaturated groups. The alcapolyenyl group is, in particular, an alcadienyl or alcatrienyl radical and preferably contains from 12–20 carbon atoms. The RCO group in which R is an alcapolyenyl group is, more particularly, the linoleoyl group.

The arbutin monoesters of formula (I) include 4-hexanoyloxyphenyl-β-D-glucose, 4-decanoyloxyphenyl-β-D-glucose, 4-dodecanoyloxyphenyl-β-D-glucose, 4-hexadecanoyloxyphenyl-β-D-glucose, 4-oleoyloxyphenyl-β-D-glucose and 4-linoleoyloxyphenyl-β-D-glucose. A mixture of these compounds can also be used.

In the depigmenting compositions of the invention, the monoesters of formula (I) must be employed in an amount which is effective to ensure the intended result. This amount can range, for example, from 0.001–10% and preferably from 0.005–5% of the total weight of the composition.

The composition containing the compounds of the invention contains a physiologically acceptable medium which is suitable for topical application, i.e. one which is compatible with the skin, the scalp and the hair, and constitutes a bleaching and/or depigmenting, cosmetic and/or dermatological composition for topical application.

The composition of the invention may be in any pharmaceutical form normally used for topical application, in particular in the form of an aqueous, aqueous-alcoholic or oily solution, an oil-in-water or water-in-oil or multiple emulsion, an aqueous or oily gel, a liquid, pasty or solid anhydrous product, a two-phase product, a dispersion of oil in an aqueous phase with the aid of spherules, these spherules possibly being polymeric nanoparticles such as nanospheres and nanocapsules or better still lipid vesicles of ionic and/or non-ionic type.

The composition may be relatively fluid and have the appearance of a white or colored cream, an ointment, a milk, a lotion, a serum, a paste or a foam. It may optionally be applied to the skin in aerosol form. It may also be in solid form and, for example, in the form of a stick.

The composition of the invention may comprise any ingredient conventionally used in the cosmetic or dermatological field, in the usual concentrations. These ingredients are selected, in particular, from fatty substances, preserving agents, gelling agents, fragrances, emulsifiers, water, antioxidants, fillers, active agents (hydrophilic or lipophilic), screening agents and mixtures thereof.

Suitable fatty substances, which may be used in the invention, include mineral oils (liquid petroleum jelly), oils of plant origin, oils of animal origin, synthetic oils (isopropyl myristate), cetylstearyl 2-ethylhexanoate, silicone oils and fluorinated oils. Fatty alcohols (2-hexyl-1-decyl alcohol, cetyl alcohol), fatty acids (stearic acid) and waxes, and mixtures thereof, may also be used.

Suitable emulsifiers which can be used in the invention, include, for example, fatty acid esters of polyethylene glycol, such as polyethylene glycol stearates, and fatty acid esters of glycerol, such as glyceryl stearate, and mixtures thereof. Mention may be made, for example, of a mixture of PEG-100 stearate and glyceryl stearate, sold under the name Arlacel 165 by the company ICI.

Suitable hydrophilic gelling agents include, in particular, carboxyvinyl polymers (carbomer), acrylic copolymers such as acrylate/alkylacrylate copolymers, polyacrylamides, polysaccharides, natural gums and clays. Suitable lipophilic gelling agents include modified clays such as bentones, metal salts of fatty acids, hydrophobic silica and polyethylenes.

Suitable moisturizers include polyols (glycerol, propylene glycol), vitamins, keratolytic agents and/or desquamating agents (salicylic acid and its derivatives, α-hydroxy acids, ascorbic acid and its derivatives), anti-inflammatory agents, calmants and mixtures thereof. In the event of incompatibility, these active agents can be incorporated into spherules, in particular ionic or non-ionic vesicles and/or nanoparticles (nanocapsules and/or nanospheres), so as to isolate them from each other in the composition.

One test demonstrates the activity of compounds of the invention as depigmenting agents, compared with the activity of kojic acid.

The test is conducted on a co-culture of keratinocytes and melanocytes by the procedure described in patent application FR 2,734,825 filed by the Applicant, and in the article by R. Schmidt, P. Krim and M. Requin, Analyses Biochimiques 235(2), 113–18, (1996).

For each test compound, the $IC_{50}$ value, i.e. the micromolar concentration ($\mu M$) for which 50% inhibition of melanogenesis is observed, is determined.

| Test compound | $IC_{50}$ |
| --- | --- |
| 4-Dodecanoyloxyphenyl-β-D-glucose | 10 $\mu M$ |
| 4-Oleoyloxyphenyl-β-D-glucose | 50 $\mu M$ |
| 4-Hexadecanoyloxyphenyl-β-D-glucose | 200 $\mu M$ |
| Kojic acid | 500 $\mu M$ |

The arbutin presents in this test, an IC50 equivalent to kojic acid.

This table shows that the compounds of formula (I) of the invention are more effective than kojic acid. In addition, they have the advantage of having no cytotoxicity with regard to keratinocytes and melanocytes, which is the major fault of the existing depigmenting agents.

Moreover, this test shows that di-O-β-glucopyranose-1, 4-hydroquinone has no depigmenting activity.

Having generally described this invention, a further understanding can be obtained by reference to certain specific examples which are provided herein for purposes of illustration only and are not intended to be limiting unless otherwise specified. The concentrations are given as a percentage by weight.

EXAMPLE 1

Oil-in-water Emulsion

| | |
| --- | --- |
| 4-hexadecanoyloxyphenyl-β-D-glucose | 0.05% |
| cetylstearyl 2-ethylhexanoate/isopropyl myristate (90/10) | 2% |
| liquid petroleum jelly | 7.5% |
| preserving agent | 0.2% |
| carboxyvinyl polymer | 0.35% |
| triethanolamine | 1.05% |
| glycerol | 3% |
| propylene glycol | 8% |
| 2-hexyl-1-decyl alcohol | 1% |
| cetyl alcohol | 0.1% |
| stearic acid | 1.4% |
| Arlacel 165 | 2% |
| water | qs 100% |

When applied daily, the cream obtained allows the skin to be bleached.

The disclosure of priority French Application No. 9708674 filed Jul. 8, 1997 is hereby incorporated by reference into the present application.

Obviously, numerous modifications and variations of the present invention are possible in light of the above teachings. It is, therefore, to be understood that within the scope of the appended claims, the invention may be practiced otherwise than as specifically described herein.

What is claimed as new and is intended to be secured by Letters Patent is:

1. A method of depigmenting, bleaching or both the human skin and/or removing pigmentation marks from the skin and/or depigmenting hair, comprising:

applying to the skin, hair or both at least one arbutin monoester of formula (I):

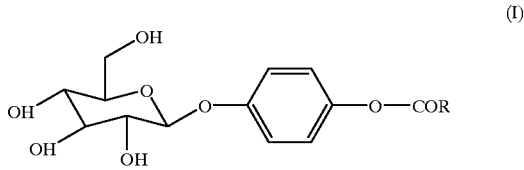

in which R is a linear or branched, satuated alkyl group containing from 5–21 carbon atoms, an alkenyl group containing from 5–21 carbon atoms or an alcapolyenyl group containing from 9–21 carbon atoms with physiologically acceptable topical excipients.

2. The method of claim 1, wherein said bleaching or depigmentation occurs by inhibiting tyrosinase and/or by ihibiting melanin-synthesis.

3. The method of claim 1, wherein R is an alkyl or alkenyl group containing from 6–18 carbon atoms.

4. The method of claim 2, wherein R is an alkyl or alkenyl group containing from 6–18 carbon atoms.

5. The method of claim 1, wherein RCO is a group selected from the group consisting of hexanoyl, decanoyl, dodecanoyl, hexadecanoyl, oleoyl and linoleoyl.

6. The method of claim 2, wherein RCO is a group selected from the group consisting of hexanoyl, decanoyl, dodecanoyl, hexadecanoyl, oleoyl and linoleoyl.

7. The method of claim 1, wherein the monoester of formula (I) is selected from the group consisting of 4-hexanoyloxyphenyl-β-D-glucose, 4-decanoyloxyphenyl-β-D-glucose, 4-dodecanoyloxyphenyl-β-D-glucose, 4-hexadecanoyloxyphenyl-β-D-glucose, 4-oleoyloxyphenyl-β-D-glucose and 4-linoleoyloxyphenyl-β-D-glucose and mixtures thereof.

8. The method of claim 2, wherein the monoester of formula (I) is selected from the group consisting of 4-hexanoyloxyphenyl-β-D-glucose, 4-decanoyloxyphenyl-βD-glucose, 4-dodecanoyloxyphenyl-β-D-glucose, 4-hexadecanoyloxyphenyl-β-D-glucose, 4-oleoyloxyphenyl-β-D-glucose and 4-linoleoyloxyphenyl-β-D-glucose and mixtures thereof.

9. The method of claim 1, wherein the monoester of formula (I) is present in the composition in an amount ranging from 0.001–10% of the total weight of the composition.

10. The method of claim 2, wherein the monoester of formula (I) is present in the composition in an amount ranging from 0.001–10% of the total weight of the composition.

11. The method of claim 1, wherein the composition further comprises at least one ingredient selected from the group consisting of fatty substances, preserving agents, gelling agents, fragrances, emulsifiers, water, antioxidants, fillers, screening agents and active agents, and mixtures thereof.

12. The method of claim 2, wherein the composition further comprises at least one ingredient selected from the group consisting of fatty substances, preserving agents, gelling agents, fragrances, emulsifiers, water, antioxidants, fillers, screening agents and active agents, and mixtures thereof.

13. The method of claim 1, wherein the ingredient is selected from the group consisting of moisturizers, vitamins, keratolytic agents and/or desquamating agents, anti-inflammatory agents and calmants, and mixtures thereof.

14. The method of claim 1, wherein the ingredient is selected from the group consisting of moisturizers, vitamins, keratolytic agents and/or desquamating agents, anti-inflammatory agents and calmants, and mixtures thereof.

* * * * *

UNITED STATES PATENT AND TRADEMARK OFFICE
CERTIFICATE OF CORRECTION

PATENT NO. : 6,306,376 B1
DATED : October 23, 2001
INVENTOR(S) : Michel Philippe It is certified that error appears in the above-identified patent and that said Letters Patent is hereby corrected as shown below:

Column 6,
Line 20, "satuated" should read -- saturated --;
Line 27, "ihibiting" should read -- inhibiting --;
Line 49, insert "-" between first "β" and "D".

Column 7,
Line 7, "Claim 1" should read -- Claim 11 --.

Column 8,
Line 3, "Claim 1" should read -- Claim 12 --.

Signed and Sealed this

Fourteenth Day of May, 2002

Attest:

Attesting Officer

JAMES E. ROGAN
Director of the United States Patent and Trademark Office